United States Patent [19]

Pallenberg

[11] Patent Number: 5,637,311
[45] Date of Patent: Jun. 10, 1997

[54] ZINC(II) COMPLEXES AND METHODS RELATED THERETO

[75] Inventor: Alexander J. Pallenberg, Duvall, Wash.

[73] Assignee: ProCyte Corporation, Kirkland, Wash.

[21] Appl. No.: 496,810

[22] Filed: Jun. 29, 1995

[51] Int. Cl.$^6$ .............................. A61F 9/02; A61K 9/70; A61K 33/32; A61K 31/44
[52] U.S. Cl. .................. 424/434; 424/433; 424/435; 424/443; 424/489; 424/641; 424/436; 514/332; 556/134; 556/135
[58] Field of Search ................................ 556/134, 135; 424/423, 641, 642, 433, 435, 436, 443, 489; 514/332

[56] References Cited

U.S. PATENT DOCUMENTS 3,980,654   9/1976   Gysling .......................... 260/270 PY
5,075,469   12/1991  Chevion ......................... 556/134

OTHER PUBLICATIONS

Duran et al., "Electrochemical Synthesis of Pyridine–2–Thionato Complexes of Zinc(II) and Cadmium(II): The Crystal Structure of 1,10–Phenanthroline–Bis(Pyridine–2–Thionato)–Zinc(II)," *Polyhedron* 10(2): 197–202, 1991.

Hu and Liu, "Structure of cis–Diaquabis(1,10–phenanthroline)zinc Sulfate Hexahydrate," *Acta Cryst.* C47:2324–2326, 1991.

Jordan et al., "Structural Dependence of the Luminescence from Bis(substituted benzenethiolato) (2,9–dimethyl–1, 10–phenanthroline)zinc(II) Complexes," *Inorg. Chem.* 30:4588–4593, 1991.

Bell et al., "Complexes of Zinc Dialkyldithiocarbamates. Part I. Complexes with Bidentate Nitrogen Ligands; Crystal Structure of 1,10–Phenanthroline Zinc Dibutyldithiocarbamate," *Inorganica Chimica Acta* 156: 205–211, 1989.

Bencini et al., "Tetracyanoquinodimethane Salts of Transition–Metal Complexes. Crystal and Molecular Structures and Magnetic Properties of Tris(1,10–phenanthroline)zinc(II) Bis(tetracyanoquinodimethanide) and Tris(1, 10–phenanthroline)copper(II) Bis(tetracyanoquinodimethanide)," *Inorg. Chem.* 28:1963–1969, 1989.

Mabrouk et al., "The Direct Electrochemical Synthesis of Zinc and Cadmium Catecholates and Related Compounds," *Inorganica Chimica Acta* 129:75–80, 1987.

Fitzgerald and Hathaway, "The Crystal Structure and Electronic Properties of the Complexes Acetatobis(1,10–phenanthroline)copper(II) Perchlorate Dihydrate, Acetatobis(1, 10–phenanthroline)copper(II) Nitrate Dihydrate, and Acetatobis(1,10–phenanthroline) zinc(II) Tetrafluoroborate Dihydrate," *J. Chem. Soc. Dalton Trans.* 141–149, 1985.

Cremers et al., "Structure of (1,10–Phenanthroline)bis(4–toluenethiolato)zinc(II)," *Acta Cryst.* B36: 3097–3099, 1980.

Monge et al., "The Adduct Zinc Dicyanide–2,9–Dimethyl–1,10–phenanthroline," *Acta Cryst.* B33:2329–2331, 1977.

Reimann et al., "The Crystal and Molecular Structure of Dicholoro(1,10–phenanthroline)zinc," *Inorganic Chemistry* 5(7):1185–1189, 1966.

*Primary Examiner*—Carlos Azpuru
*Attorney, Agent, or Firm*—Seed and Berry LLP

[57] ABSTRACT

Zinc(II) complexes and methods relating thereto are disclosed. The zinc(II) complexes comprise a zinc(II) ion complexed by a multi-dentate ligand. Methods of this invention include the use of the zinc(II) complexes as anti-viral agents and/or as anti-inflammatory agents. Methods of this invention also include inhibition of viral infection, as well as inhibiting transmission of sexually transmitted diseases. Exemplary zinc(II) complexes include zinc(II):neocuproine (2:1) and zinc(II):bathocuproine disulfonic acid (2:1).

5 Claims, 2 Drawing Sheets

ZINC(II) COMPLEXES AND METHODS RELATED THERETO

TECHNICAL FIELD

This invention is generally directed to zinc(II) complexes and methods relating to the use thereof and, more specifically, to zinc(II) complexed by a multi-dentate ligand.

BACKGROUND OF THE INVENTION

Zinc is found in both plants and animals and over 100 zinc-containing proteins and enzymes have been identified (Chaney, *Textbook of Biochemistry with Clinical Correlations*, pp. 1115–1147, Devlin (ed.), New York, New York, Wiley-Liss, 1992). Examples of zinc-containing enzymes include carbonic anhydrase (hydration of carbon dioxide in red blood cells), carboxypeptidase A (pancreatic peptidase), NAD-dependent dehydrogenases (alcohol dehydrogenase in liver), leucine aminopeptidase (peptidase in kidney and gastric mucosa), pyruvate carboxylase (citric acid cycle component), and leukotriene A4 hydrolase (synthesis of lipid mediators in neutrophils) (White et al., *Principles of Biochemistry*, New York, N.Y. McGraw-Hill Book Company, 1973). Zinc also serves as an important structural component of many proteins such as DNA binding proteins in a structure commonly termed "zinc fingers" (Schultz et al., *Textbook of Biochemistry with Clinical Correlations*, pp. 91–134, Devlin (ed.), New York, N.Y., Wiley-Liss, 1992).

Zinc compounds, primarily zinc salts, have shown utility in a number of areas. Examples are wound healing (Agren, *Acta. Derm. Venereol. Supp. (Stockh)* 154: 1–36, 1990; Pastorfide et al., *Clin. Ther.* 11: 258–63, 1989), healing of gastric ulcers (Frommer, *Med. J. Aust.* 2: 793– 96, 1975), inhibition of leukotriene A4 hydrolase (prevention of the formation of lipid mediators of inflammation) (Wetterholm et al., *Arch. Biochem. Biophys.* 311: 263–71, 1994), and the inhibition of certain viruses such as human immunodeficiency virus (HIV) (Bridget et al., *J. Med. Chem.* 38: 366–78, 1995), inhibition of the HIV protease (Zhang et al., *Biochemistry* 30: 8717–21, 1991), herpes virus (Kumel et al., *J. Gen. Virol.* 71: 2989–97, 1990; Fridlender et al., *Virology* 84: 551–54, 1978; Gordon et al., *Antimicrob. Agents Chemother.* 8: 377–80, 1975), vaccinia virus (Katz et al., *Antimicrob. Agents Chemother.* 19: 213–17, 1981; Zaslavsky et al., *J. Virol.* 29: 405–48, 1979), foot and mouth disease virus (Firpo et al., *Arch. Virol.* 61: 175–81, 1979), and rhino virus(Korant et al., *J. Virol.* 71: 2989–97, 1976).

In addition to zinc(II) salts, a number of zinc(II) complexes have been made and characterized. However, in most instances such zinc(II) complexes have merely been studied to determine the coordination geometry of the metal, or luminescence thereof. For example, Jordan et al. (*Inorg. Chem.* 30: 4588–93, 1991) report the structural dependence of the luminescence from bis(substituted benzenethiolato) (2,9-dimethyl-1,10-phenanthroline) zinc(II) coplexes, while Monge (*Acta Cryst. B33*: 2329–31, 1977) reports the crystal structure of a (dicyanide)(2,9-dimethyl-1,10-phenanthroline) zinc(II) complex. Other researchers have reported zinc(II) complexes with 1,10-phenanthroline, but not for use as biologically active compounds (Fitzgerald et al., *J. Chem. Soc. Dalton Trans.* 141–49, 1985; Romero et al., *Polyhedron* 10: 197–202, 1991; Bell et al. (*Inorganica Chimica Acta.* 156: 205–11, 1989; Reimann et al., *Inorg. Chem.* 5: 1185–89, 1966; Bencini et al., *Inorg. Chem.* 28: 1963–69, 1989; Hu and Liu, *Acta Cryst. C47*: 2326–33, 1991; Cremers et al., *Acta Cryst. B36*: 3097–99, 1980).

While the use of zinc salts appear promising for use in certain therapeutic areas, there is still a need in the art for additional zinc-containing compounds, complexes or compositions which possess biological activity. The present invention fulfills this need, and provides further related advantages.

SUMMARY OF THE INVENTION

This invention is generally directed to zinc(II) complexes and methods relating thereto. More specifically, the zinc(II) complexes of the present invention comprise zinc(II) complexed by a multi-dentate ligand.

The zinc(II) complexes have utility for the inhibition of lipid mediators of inflammation, and for inhibiting viral activity and infection, including (but not limited to) HIV replication in an HIV-infected animal. Methods of the present invention comprise administering to an animal in need thereof an effective amount of a zinc(II) complex.

Other aspects of this invention will become evident upon reference to the attached figures and following detailed description. All references identified herein are hereby incorporated by reference in their entirety

DETAILED DESCRIPTION

This invention is generally directed to zinc(II) complexes. Zinc is almost always found in the +2 oxidation state, in which it is invariably quite stable. (See, generally, Cotton and Wilkinson, *Advanced Inorganic Chemistry*, 5th ed., John Wiley & Sons, New York, pp. 503–527, 1988). Zinc(II) has previously been reported to have four coordination sites, and to generally possess a tetrahedral configuration.

In general, chelating agents are coordination compounds in which a single ligand occupies more than one coordination position of a metal ion. If the ligand occupies two coordination positions, it is considered a bi-dentate ligand; if more than two coordination positions are occupied by the ligand, it is considered a poly-dentate ligand (such as a tri-dentate ligand or a tetra-dentate ligand). As used herein, a "multi-dentate ligand" is a bi-, tri- or tetra-dentate ligand which occupies two, three or four coordination sites, respectively, of zinc(II).

Any multi-dentate ligand which chelates zinc(II) to yield a zinc(II) complex is suitable in the practice of this invention. However, in a preferred embodiment, the multi-dentate ligands of this invention are selected from the following general structures I through VII:

I wherein A and B represent heteroatoms which may occupy coordination sites of zinc(II), and are preferably selected from nitrogen, oxygen, sulfur and phosphorous.

The rings of structures I through VII may be aromatic, non-aromatic or a mixture of both aromatic and non-aromatic rings. For example, the following structures are representative of such combinations:

Ia

Representative examples of multi-dentate ligands of this invention having structures I through VII are set forth in Table 1. Specifically, Table 1 identifies the structure of the representative multi-dentate ligand, lists the corresponding chemical name, identifies the Chemical Abstracts Registration Number ("CA Reg. No."), and provides a corresponding reference (if available) describing the synthesis and/or chemistry of the identified multi-dentate ligand.

TABLE 1

| Structure | Name | CA Reg. No. | Reference |
|---|---|---|---|
|  | benzo (2,1-b:3,4-b) dithiophene | 211-53-0 | Sturaro et al., Heterocycl. Chem. 27:1867, 1990 |
|  | benzo (2,1-b:3,4-b) difuran | 211-47-2 | Rene et al., Eur. J. Med. Chem.-Chim. Ther. 13:435, 1978 |

TABLE 1-continued

| Structure | Name | CA Reg. No. | Reference |
|---|---|---|---|
| | thieno (3,2-g) benzofuran | 438-31-9 | Cagniant and Kirsch, Hebd. Seances Acad. Sci. C. 282: 465, 1976 |
| | 2H-furo (3,2-g) indole | 103671-62-1 | Lawrence Jr., Eur. Pat. Appl. EP 173,520, 1986 |
| | 2H-benzo (2,1-b:3,4-b') dipyrrole | 112149-08-3 | Berlin et al., J. Chem. Soc. Chem. Commun. (15):1176, 1987 |
| | 1H-cyclopenta (2,1-b:3,4-b') bipyridine | 42262-29-3 | |
| | 1,10-phenanthroline | 66-71-7 | |
| | furo (3,2-h) quinoline | 234-28-6 | |
| | 2,2'-bipyridyl | 366-18-7 | |

In structures I through VII above, further ring substitutions with heteroatoms are permitted. Preferably, such heteroatoms are selected from nitrogen, oxygen, sulfur, and phosphorus. For example, the compounds listed in Table 2 illustrate further representative multi-dentate ligands of the present invention having additional ring substitutions. As with Table 1, Table 2 identifies the structure of the representative multi-dentate ligands, lists the corresponding chemical name, identifies the CA Reg. No., and provides a corresponding reference (if available) describing the synthesis and/or chemistry of the identified multi-dentate ligand.

TABLE 2

| Structure | Name | CA Reg. No. | Reference |
|---|---|---|---|
| | furano (3,2-g) benzoxazole | 25885-39-6 | |

TABLE 2-continued

| Structure | Name | CA Reg. No. | Reference |
|---|---|---|---|
| | furano (2,3-e) benzoxazole | 66037-80-1 | Turin et al., Fr. Demande 2,338,041, 1977 |
| | thieno (3,2-g) benzoxazole | 58188-85-5 | Iddon et al., J. Chem. Soc., Perkin Trans. I 17:1686, 1975 |
| | thieno (3,2-g) benzothiazole | 72121-58-5 | |
| | thieno (2,3-e) benzothiazole | 211-36-9 | |
| | benzo (1,2-d:3,4-d') bis (1,3) dioxide | 211-50-7 | Dallacker and Weiner, Justus Liebigs Ann. Chem. 725:99, 1969 |
| | benzo (1,2-d:3,4-d') diimidazole | 211-10-9 | |
| | pyrrolo (2,3-e) benzimidazole | 53068-46-5 | Chetverikov et al., U.S.S.R. 425,906, 1974 |
| | benzo (2,1-d:3,4-d') bis (1,3) oxathiole | 211-54-1 | |
| | 2H-imidazo (4,5-e) benzothiazole | 42341-40-2 | |
| | 2H-imidazo (4,5-g) benzothiazole | 211-23-4 | |

TABLE 2-continued

| Structure | Name | CA Reg. No. | Reference |
|---|---|---|---|
| | 1,3-dioxolo (4,5-e) benzothiazole | 77482-58-7 | Foerster et al., Ger. Offen. 2,903,966, 1980 |
| | benzo (1,2-d:3,4-d') bisthiazole | 211-37-0 | |
| | benzo (2,1-d:3,4-d') bisthiazole | 23147-19-5 | |
| | benzo (1,2-d:4,3-d') bisthiazole | 10558-80-2 | Grandolini et al., Ann. Chim. 58:91, 1968 |
| | thiazolo (5,4-e) benzoxazole | 211-35-8 | |
| | thiazolo (5,4-g) benzoxazole | 51273-21-3 | |
| | thiazolo (4,5-e) benzoxazole | 315-47-9 | |
| | thiazolo (4,5-f) benzoxazole | 67239-73-0 | Fridman et al., Ikr. Khim. Zh. 44:399, 1978 |
| | benzo (2,1-d:3,4-d') bisoxazole | 211-19-8 | |
| | benzo (1,2-d:3,4-d') bisoxazole | 211-20-1 | |

TABLE 2-continued

| Structure | Name | CA Reg. No. | Reference |
|---|---|---|---|
| | benzo (1,2-d:4,3-d') bisoxazole | 54935-19-2 | Barker et al., J. Chem. Res. Synop. (9):328, 1986 |
| | furo (2,3-d) thieno (3,2-b) pyridine | 110665-19-5 | |
| | 1H-imidazo (4,5-d) thieno (3,2-b)-pyridine | 111163-54-3 | Takada et al., Eur. Pat. Appl. EP 223,420, 1987 |
| | dithieno (3,2-b:2',3'-d) pyridine | 40826-38-8 | Yang et al., Synthesis 2:130, 1989; Heeres et al., Syn. Commun. 2:365, 1972 |
| | 5H-oxazolo (4,5-e) thiazolo (3,2-c) pyrimidine | 211-46-1 | |
| | dithieno (3,2-c:2',3'-e) pyridazine | 51974-92-6 | Nonciaux et al., Bull. Soc. Chim. Fr. 12 Pt 2, 3318, 1973 |
| | 1H-(1,2,4) triazolo (5,1-b) purine | 387-96-2 | |
| | bis (1,2,4) triazolo (1,5-d:5',1'-c) pyrazine | 55366-22-8 | Vercek et al., Tetrahedron Lett. (51/52):4539, 1974 |
| | benzo (2,1-b:3,4-b') dipyran | 231-29-8 | Monatsch 80:743, 1949 |

TABLE 2-continued

| Structure | Name | CA Reg. No. | Reference |
|---|---|---|---|
| | benzo (1,2-b:4,3-b') bis (1,4)-oxathiin | 231-34-5 | |
| | benzo (1,2-e:3,4-e') dipyrazine | | |
| | benzo (1,2-d:3,4-d') diimidazole | 211-10-9 | |
| | pyrazino (2,3-f) quinoxaline | 231-23-2 | Shim et al., Synthesis 2:116, 1980; Nasielski-Hinkins et al., J. Chem. Soc. Perkin Trans. 1:1229, 1975 |
| | bis (1,2,4) oxadiazolo (2,3-d:3', 2'-c) pyrazine | 74382-83-5 | |
| | (1,2,4)-oxadiazolo (3,2-i) purine | 56248-95-4 | Miura et al., Chem. Pharm. Bull. 23:464, 1975 |
| | bis (1,2,4) triazolo (1,5-b:5',1'-f) pyridazine | 51519-32-5 | Polanc et al., J. Org. Chem. 39:2143, 1974 |
| | bis (1,2,4) triazolo (1,5-d:1', 5'-c) pyrimidine | 76044-62-7 | Brown and Shinozuka, Aust. J. Chem. 33:1147, 1980 |

General structures I through VII identified above may possess further chemical moieties covalently attached to the structural backbone, as illustrated below:

Ib

IIb cyclic or noncyclic, saturated or unsaturated, substituted or unsubstituted carbon chain containing from 1–20 carbon atoms; and an "aryl moiety" is a straight chain or branched, cyclic or noncyclic, saturated or unsaturated, substituted or unsubstituted carbon chain containing at least one substituted or unsubstituted aromatic moiety and containing from 6–20 carbon atoms. Such chemical moieties may also be covalently attached to the ring fusion atoms. Representative examples of the chemical moieties of this invention include, but are not limited to, the moieties identified in Table 3 below.

TABLE 3

| | | |
|---|---|---|
| —H | —CH$_3$ | —CH$_2$Br |
| —CH$_2$OH | —CH$_2$Cl | —CBr$_3$ |
| —CH$_2$C$_6$H$_5$ | —C$_6$H$_5$ | —(CH$_2$)$_{1-12}$CH$_3$ |
| —Cl | —CHO | —COOH |
| —COOMe | —CH=NOH | —CH$_2$NH$_2$ |
| —CH$_2$C≡CH | —CH=CH$_2$ | —P(C$_6$H$_5$)$_2$ |
| —CH$_2$CH(CO$_2$H)$_2$ | —CON(CH$_2$COOH)$_2$ | —CH$_2$N(CH$_2$COOH)$_2$ |
| $\begin{array}{c}-CH_2\\|\\N\diagdown CH_2OH\\\diagup\quad\quad H\end{array}$ | $\begin{array}{c}\quad\ CH_3\\\quad\ \|\\-N-CH-CH-C_6H_5\\\ \|\quad\quad\ \|\\\ CH_3\quad\ OH\end{array}$ | $\begin{array}{c}-CH_2N(CH_2)_{11}CH_3\\\|\\CH_3\end{array}$ |
| —Ph—SO$_3$Na | | | wherein R$_1$ through R$_8$ are the same or different, and are selected from the following chemical moieties: —H, —OH, —X, —OX, —XOH, —COOH, —COOX, —CHO, —CXO, —F, —Cl, —Br, —I, —CN, —NH$_2$, —NHX, —NX$_2$, —PX$_2$, —SO$_3$H, —SO$_3$Na, —SO$_3$K, —SO$_3$X, —PO$_3$H, —OPO$_3$H, —PO$_3$X, —OPO$_3$X and —NO$_2$. As used herein, "X" represents and an alkyl moiety or an aryl moiety. An "alkyl moiety" is a straight chain or branched, Representative examples of the multi-dentate ligands possessing further chemical moieties covalently attached to the structural backbone of structures I through VII are presented in Table 4. In particular, Table 4 identifies the structure of the representative multi-dentate ligands, lists the corresponding chemical name, identifies the CA Reg. No., and provides a corresponding reference (if available) describing the synthesis and/or chemistry of the multi-dentate ligand.

TABLE 4

| Structure | Name | CA Reg. No. | Reference |
|---|---|---|---|
| (structure) | 2,2'-bipyridine-4,4'-dicarboxylic acid | 6813-38-3 | |
| (structure) | 2,2'-bis (4,5-dimethylimidazole) | 69286-06-2 | J. Organomet. Chem. 307:39, 1986 |
| (structure) | 2,3-bis (2-pyridyl) pyrazine | 25005-96-3 | (Aldrich: 28,164-16) |
| (structure) | 5,5'-dimethyl-2,2'-bithiophene | 16303-58-5 | |
| (structure) | 6,6'-dimethyl-2,2'-dipyridine | 4411-80-7 | Kauffmann et al., Chem. Ber. 109:3864, 1976 |

The chemical moieties covalently attached to the structural backbone may be joined to yield an aromatic or nonaromatic cyclic chemical moiety. Representative examples of such cyclic chemical moieties are set forth in Table 5, which identifies the structure of the representative multi-dentate ligands, lists the corresponding chemical name, identifies the CA Reg. No., and provides a corresponding reference (if available) describing the synthesis and/or chemistry of the multi-dentate ligand.

TABLE 5

| Structure | Name | CA Reg. No. | Reference |
|---|---|---|---|
| (structure) | 6,7-dihydro-5,8-dimethyl dibenzo (b) (1, 10) phenanthroline | 5298-71-5 | |
| (structure) | bibenzimidazole | 123067-51-6 | |
| (structure) | 2,2'-bisquinoline | 119-91-5 | (Aldrich: B3,540-7) |

The synthesis of representative examples of the multi-dentate ligands of this invention are disclosed in Table 6 and Table 7 below. Specifically, in these tables the structure of the multi-dentate ligands are identified along with their CA

TABLE 6

Synthesis of Ligands for Representative Zinc (II) Complexes Having the Structure:

(R2 through R7 = hydrogen, unless indicated)

| R1 | R8 | CA Reg. No. | Reference |
|---|---|---|---|
| $-CH_3$ | $-CH_3$ | 484-11-7 | O'Reilly et al., Aust. J. Chem. 13:145, 1960 |
| $-CH_2Br$ | $-CH_2Br$ | 78831-37-5 | Weijen et al., J. Org. Chem. 57:72358, 1992; Jukkala et al., Helv. Chim. Acta. 75:1621, 1992; Chandler et al., J. Heterocycl. Chem. 18:599, 1981 |
| $-CH_2Br$ | $-CH_2OH$ | 142470-16-4 | Weijen et al., J. Org. Chem. 57:7258, 1992 |
| $-CBr_3$ | $-CBr_3$ | | Chandler et al., J. Heterocycl. Chem. 18:599, 1981 |
| $-CH_2Cl$ | $-CH_2Cl$ | | Newkome et al., J. Org. Chem. 50:3807, 1985; Newcome et al., J. Org. Chem. 48:5112, 1983 |
| $-CCl_3$ | $-CCl_3$ | | Chandler et al., J. Heterocycl. Chem. 18:599, 1981; Newcome et al., J. Org. Chem. 48:5112, 1983 |
| $-CN$ | $-CN$ | 57709-63-4 | Chandler et al., J. Heterocycl. Chem. 18:599, 1981; Sjoegren et al., Organometallics 11:3954, 1992 |
| $-CH_2C_6H_5$ | $-CH_2C_6H_5$ | 223-20-1 | Sjoegren et al., Organometallics 11:3954, 1992 |
| $-(CH_2)_{11}CH_3$ | $-(CH_2)_{11}CH_3$ | | Menger et al., J. Am. Chem. Soc. 113:4017, 1991 |
| $-(CH_2)_3CH_3$ | $-(CH_2)_3CH_3$ | 85575-93-5P | Sugihara et al., JP 02096578 A2, Jpn. Kokai Tokkyo Koho 113(15):132159v |
| ($R_3 = R_6 = H$, Ph $-(CH_2)_3CH_3$ | $-(CH_2)_3CH_3$ | | Delton et al., EP 339973 A1, Eur. Pat. Appl. 112(21):19835p, 1989 |
| ($R_4 = R_5 = -CH_3$) $-Cl$ | $-Cl$ | 29176-55-4 | Sjoegren et al., Organometallics 11:3954, 1992; Delton et al., EP 33993 A1, Eur. Pat. Appl. 112(21):19835p, 1989 |
| $-CH_2OH$ | $-CH_2OH$ | 78831-36-4 | Chandler et al., J. Heterocycl. Chem. 18:599, 1981; Delton et al., EP 339973 A1, Eur. Pat. Appl. 112(21):19835p, 1989; Newcome et al., J. Org. Chem. 48:5112, 1983 |
| $-CHO$ | $-CHO$ | 57709-62-3 | Ziessel, Tetrahedron Lett. 30:463, 1989; Toner, EP 288256 A2, Eur. Pat. Appl. 111(15):130322c; Bell et al., J. Inclusion Phenom. 5:149, 1987 |
| $-COOH$ | $-COOH$ | | Chandler et al., J. Heterocycl. Chem. 18:599, 1981 |
| $-COOMe$ | $-COOMe$ | | Chandler et al., J. Heterocycl. Chem. 18:599, 1981; Newcome et al., J. Org. Chem. 48:5112, 1983 |
| $-CH=NOH$ | $-CH=NOH$ | | Chandler et al., J. Heterocycl. Chem. 18:599, 1981 |
| $-CH_2NH_2$ | $-CH_2NH_2$ | | Chandler et al., J. Heterocycl. Chem. 18:599, 1981 |

TABLE 6-continued

Synthesis of Ligands for Representative Zinc (II) Complexes Having the Structure:

(R2 through R7 = hydrogen, unless indicated)

| R1 | R8 | CA Reg. No. | Reference |
|---|---|---|---|
| —CHO | —H | 33795-37-8 | Toner, EP 288256 A2, Eur. Pat. Appl. 111(15):130322c |
| —COOH | —H | 1891-17-4 | Toner, EP 288256 A2, Eur. Pat. Appl. 111(15):130322c |
| —$CH_2C\equiv CH$ | —$CH_2C\equiv CH$ | | Sjoegren et al., Organometallics 11:3954, 1992 |
| —$C_6H_5$ | —$C_6H_5$ | | Dietrich-Buchecker et al., Tetrahedron Lett. 23:5291, 1982 |
| —Cl | —$CH_3$ | | Newcome et al., J. Org. Chem. 54:1766, 1989 |
| —CH=$CH_2$ | —CH=$CH_2$ | | Newkome et al., J. Org. Chem. 50:3807, 1985 |
| —$P(C_6H_5)_3$ | —$P(C_6H_5)_3$ | | Ziessel, Tetrahedron Lett. 30:463, 1989 |
| $CH_2CH(CO_2H)_2$ | —$CH_2CH(CO_2H)_2$ | | Newcome et al., Inorg. Chem. 24:811, 1985 |
| —$CH_2N(CH_2)_{11}CH_3$ \| $CH_3$ | —$CH_2$-N(pyrrolidine-CH_2OH,H) | | Weijen et al., J. Org. Chem. 57:7258, 1992 |
| —$CH_2$-N(pyrrolidine-CH_2OH,H) | —$CH_2$-N(pyrrolidine-CH_2OH,H) | | Weijen et al., J. Org. Chem. 57:7258, 1992 |
| —$CH_2OH$ | —$CH_2$-N(pyrrolidine-CH_2OH,H) | | Weijen et al., J. Org. Chem. 57:7258, 1992 |
| —$CH_2N(CH_2)_{11}CH_3$ \| $CH_3$ | —N($CH_3$)—CH—CH($C_6H_5$)—OH | | Weijen et al., J. Org. Chem. 57:7238, 1992 |
| —$CH_2N(CH_2COOH)_2$ | —$CH_2N(CH_2COOH)_2$ | | Mukkala et al., Helv. Chim. Acta 75:1621, 1992; Toner, EP 288256 A2, Eur. Pat. Appl. 111(15):130322c |
| —$CON(CH_2COOH)_2$ | —$CON(CH_2COOH)_2$ | | Toner, EP 288256 A2, Eur. Pat. Appl. 111(15):130322c |
| —$CH_3$ ($R_3 = R_6 =$ —Ph—$SO_3Na$) | —$CH_3$ | 52698-84-7 | Blair et al, Talanta 7:163, 1961 |

TABLE 7

Synthesis of Representative Zinc (II) Complexes Having the Structure:

($R_2$ through $R_7$ = hydrogen, unless indicated)

| R1 | R8 | CA Reg. No. | Reference |
|---|---|---|---|
| —CN | —CN | 4411-83-0 | Sjoegren et al., Organometallics 11:3954, 1992 |
| —$CH_2Cl$ | —$CH_2Cl$ | 74065-64-8 | Bell et al., J. Inclusion Phenom. 5:149, 1987 |
| —CHO | —CHO | | Newkome et al., J. Org. Chem. 50:3807, 1985 |
| —CH=$CH_2$ | —CH=$CH_2$ | | Newkome et al., J. Org. Chem. 50:3807, 1985 |
| ($R_1$ and $R_2$ = benzo moiety) | ($R_7$ and $R_8$ = benzo moiety) | 119-91-5 | (Aldrich: B3,540-7) |

In one embodiment of this invention, the multi-dentate ligands are selected from the following structures:

Ic

IIc wherein $R_1$ through $R_8$ are the same or different, and are selected from hydrogen, an alkyl moiety and an aryl moiety.

In a preferred embodiment, the multi-dentate ligand is 6,6'-dimethyl-2,2'-dipyridine having structure Id:

Id

In a further preferred embodiment, the multi-dentate ligand is neocuproine (2,9-dimethyl-1,10-phenanthroline) having structure IId, or is bathocuproine disulfonic acid ("BCDS") having one of the isomeric structures IIe, IIe', IIe" or IIe''':

IId

IIe

(para, para)

IIe'

(meta, para)

-continued (meta, meta)

(ortho, meta)

Unless otherwise indicated, BCDS refers to a physical mixture of the above isomers (i.e., IIe, IIe', IIe" and IIe'"). Typically, the ratio of the various isomers (i.e., IIe:IIe':IIe") vary depending upon the commercial source of BCDS as follows: Aldrich Chemical Co., Inc. (Milwaukee, Wis.) 9.1:38.6:41.2; Spectrum Chemical Manufacturing Corp. (Gardena, Calif.) 8.5:39.7:45.2; GFS Chemicals (Columbus, Ohio) 8.4:38.5:45.3; Janssen Pharmaceutica (subsidiary of Johnson & Johnson) (Beerse, Belgium) 4.6–8.7:36.4–39.4:44.4–55.9; with the IIe'" isomer present in commercial sources in only trace amounts (i.e., typically about 1%).

As discussed above, zinc(II) complexes of this invention may be made by contacting a multi-dentate ligand with a zinc(II) source. The multi-dentate ligands may be obtained from commercial sources, or may be synthesized by known organic synthesis techniques from commercially available reagents. Preferably, water soluble multi-dentate ligands are complexed with the zinc(II) in aqueous solution, employing $Zn(NO_3)_2$ or $Zn(SO_4)$ as the zinc(II) source. The resulting zinc(II) complex may then be recovered by evaporation of solvent to yield the zinc(II) complex. Alternatively, if the multi-dentate ligand is not readily soluble in water, zinc(II) complexes may be formed by the above procedure employing a suitable non-aqueous (e.g., organic) solvent.

In the practice of this invention, the ratio of the multi-dentate ligand to zinc(II) may be any ratio which results in a zinc(II) complex. Preferably, the ligand to zinc ratio is at least 1:1, and more preferably at least 2:1. In a further embodiment, the ligand to zinc(II) ratio ranges from 1:1 to 3:1 (including 2:1). Such zinc(II) complexes may be made by the procedures identified in the preceding paragraph by reacting the appropriate molar ratios of the multi-dentate ligand and the zinc(II) ion source.

In the case of zinc(II):neocuproine, the molar ratio of zinc to neocuproine is preferably in excess of 1:1, and more preferably at least 2:1.

When administered to an animal for therapeutic, prophylactic or cosmetic purposes, the zinc(II) complexes of this invention may be readily formulated by techniques known to those skilled in the art. (Preferred zinc(II) complexes of this invention are colorless, which is highly desirable for consumer appeal and acceptance.) For example, the zinc(II) complexes may be combined with one or more suitable carriers or diluents to yield a pharmaceutical preparation suitable for topical, oral or parenteral application- Such diluents or carriers, however, should not interact with the zinc(II) complex to significantly reduce the effectiveness thereof. Effective administration will preferably deliver a dosage of approximately 0.01 to 100 mg of the zinc(II) complex per kg of body weight.

Methods for encapsulating compositions (such as in a coating of hard gelatin) for oral administration are well known in the art (see, e.g., Baker, Richard, *Controlled Release of Biological Active Agents*, John Wiley and Sons, 1986)(incorporated herein by reference). Suitable carriers for parenteral application (such as intravenous, subcutaneous or intramuscular injection) include sterile water, physiological saline, bacteriostatic saline (saline containing 0.9 mg/ml benzyl alcohol) and phosphate-buffered saline. The zinc(II) complexes may be topically applied in the form of liquids, containing acceptable diluents (such as saline and sterile water) or may be applied as lotions, creams or gels, containing additional ingredients to impart the desired texture, consistency, viscosity and appearance. Such additional ingredients are familiar to those skilled in the art and include emulsifying agents such as non-ionic ethoxylated and nonethoxylated surfactants, fatty alcohols, fatty acids, organic or inorganic bases, preserving agents, wax esters, steroid alcohols, triglyceride esters, phospholipids such as lecithin and cephalin, polyhydric alcohol esters, fatty alcohol esters, hydrophilic lanolin derivatives, hydrophilic beeswax derivatives, hydrocarbon oils such as palm oil, coconut oil, mineral oil, cocoa butter waxes, silicon oils, pH balancers and cellulose derivatives.

Topical administration may by accomplished by applying an amount of the preparation directly to the desired area. The required dosage will vary according to the particular condition to be treated, the severity of the condition, and the duration of the treatment. Preferably, when the zinc(II) complex is topically applied in the form of a lotion, cream or gel, the preparation may contain about 1% to about 20% of a penetration enhancing agent. Examples of penetration enhancing agents include dimethylsulfoxide (DMSO), urea and eucalyptol. In the case of a liquid preparations for topical application, the concentration of penetration enhancing agent (such as DMSO) may comprise about 30% to about 80% of the preparation.

The zinc(II) complexes of the present invention posses utility as anti-viral agents, and are particularly effective in the inhibition of the AIDS virus. Human acquired immunodeficiency syndrome or "AIDS" is a fatal disease for which there is presently no cure. The disease is believed to be caused by a virus known as the human immunodeficiency virus, commonly referred to as "HIV." The virus is transmitted by HIV-infected individuals through the exchange of bodily fluids. HIV infection results most commonly from sexual contact with an infected partner and the sharing among intravenous drug users of hypodermic syringes previously used by an infected individual. A pregnant HIV-infected mother may infect her unborn child by transplacental transmission, and HIV-contaminated blood is a possible source of infection for individuals subject to blood transfusion.

HIV infection causes a suppression of the immune system. The immune suppression renders the infected individual vulnerable to a variety of opportunistic infections and conditions that are otherwise kept in balance by a healthy immune system. Fatalities result from HIV infection due to the inability of AIDS patients to respond to treatment of the opportunistic infections and conditions as a consequence of their compromised immune systems. Because the virus may often remain dormant, the manifestation of AIDS from HIV infection may take as long as ten years.

One approach to the treatment of AIDS has targeted the opportunistic infections or conditions which result from HIV infection. The treatment of such infections or conditions, however, is ultimately ineffective and, while prolonging the life of the infected individual, does not treat the underlying HIV infection. A second approach to the treatment of AIDS targets the cause of the disease itself. Because AIDS results from viral infection, it is believed that viral inactivation may ultimately provide a cure. (Materials which are capable of viral inactivation or inhibition are referred to herein as "antiviral agents.")

To understand the mode of action of antiviral agents in the treatment of AIDS, an understanding of the process of HIV infection is necessary. HIV chronically infects specific immune cells known as T-helper cells, which are required for normal immune response. The HIV infected T-helper cells serve as hosts to the virus and facilitate the reproduction of the virus (the process of viral reproduction is commonly referred to as "replication"). After HIV infection, the infected host cell eventually dies, the replicated HIV virus is released, and the infection spreads to additional cells. This cycle continues unabated, depleting the population of T-helper cells and, in time, weakens the immune system to the onset of AIDS symptoms. Because T-helper cells are continuously produced by the body, the population of these cells may be reestablished in the absence of further HIV infection. Therefore, the progression of HIV infection (and the subsequent onset of AIDS) may be arrested by the prevention or inhibition of viral replication, and antiviral agents capable of inhibiting or preventing the replication of HIV should be effective in the treatment of AIDS.

At the genetic level, HIV replication requires the insertion of vital deoxyribonucleic acid ("DNA") into the genome of the host cell. The genome of the host cell consists of the cell's own DNA, and is responsible for the synthesis of materials essential to the cell's own function and proliferation. Once the viral DNA is inserted into the host genome, the host facilitates replication of HIV. The inserted viral DNA is an enzymatic product derived from vital ribonucleic acid ("RNA") and the action of an enzyme known as HIV reverse transcriptase. Inhibition of HIV reverse transcriptase precludes the formation of viral DNA required for insertion into the genome of the host. Vital replication is prevented by the absence of vital DNA in the host cell genome. Antiviral agents which inhibit HIV reverse transcriptase are thus potential therapeutic drugs for treatment of AIDS.

Accordingly, in yet another embodiment of the present invention, antiviral agents are disclosed for inhibiting HIV replication, as well as methods relating to the administration thereof to an HIV-infected patient. The antiviral agents of this invention are the zinc(II) complexes discloses above, and the methods include administration of a therapeutically effective amount of a composition which includes a zinc(II) complex in combination with a pharmaceutically acceptable carrier or diluent. Although not limited by the following theory, the zinc(II) complexes of this invention may enhance transport of zinc(II) into HIV infected cells which, in turn, may inhibit or inactivate the HIV protease and thus inhibit the replication of HIV. As used herein, the term "HIV" includes the various strains of the virus (such as HIV-1 and HIV-2).

Administration of the zinc(II) complexes of the present invention may be accomplished in any manner which will result in a systemic dose of a therapeutically effective amount of the zinc(II) complex to an HIV-infected animal or patient (including human patients). For example, such administration may be by injection (intramuscular, intravenous, subcutaneous or intradermal), oral, nasal, or suppository applications. Typically, preparations of the present invention include zinc(II) complexes in solution for various forms of injection, or in preparations which are formulated for the sustained release of the zinc(II) complexes for oral, nasal, or suppository dosage application and generally include one or more inert, physiological acceptable carriers. As used herein, the term "effective amount" means an amount of the zinc(II) complex which inhibits HIV replication in the patient. Suitable dosages may range from approximately 0.01 to 100 mg of zinc(II) complex per kg body weight.

The zinc(II) complexes of this invention may be screened for their ability to inhibit HIV replication using known techniques. For example, HIV virus replication may be monitored using the Cytopathic Effect (CPE) assay disclosed by Bergeron et al. (*J. Virol.* 66: 5777–5787, 1992). In this assay, the degree of infection is monitored by the appearance of fused cellular membranes ("syncitium"). Alternatively, assays directed to activity of HIV protease may be employed. For example, the assays and techniques disclosed in the following references may be employed: Ashorn et al., *Proc. Natl. Acad. Sci. U.S.A.* 87: 7472–7476, 1990; Schramm et al., *Biochem. Biophys. Res. Commun.* 179: 847–851, 1991; Sham et al., *Biochem. Biophys. Res. Commun.* 175: 914–919, 1991; and Roberts et al., *Science* 248: 358–361, 1990.

Inhibition of viral replication by the zinc(II) complexes of this invention may also be due to inhibition and/or prevention of viral entry into a cell. With respect to HIV, for example, the zinc(II) complexes may prevent viral entry by interfering with CD4 receptor binding and membrane fusion. This may be illustrated by observing the inhibitory effect of a zinc(II) complex of this invention on syncytium formation using a virus-free, genetically engineered syncytium formation assay (Fu et al., *J. Virol.* 7: 3818, 1993). This assay relies upon the molecular recognition of gp120, gp41 and the CD4 receptor to create syncytium. Inhibition of syncytium formation in this assay indicates that the zinc(II) complexes inhibit HIV replication by preventing viral entry, presumably by interacting with the viral proteins gp120 and gp41, and thus prevent and/or inhibit gp120 and gp41 function related to viral binding and membrane fusion. Thus, the zinc(II) complexes of the present invention have utility in preventing and/or inhibiting the spread of HIV to uninfected cells.

Accordingly, in this aspect of the present invention, zinc(II) complexes may be formulated in a manner suitable for application to, for example, the vaginal or rectal mucosa, as well as the penis. Suitable formulations include, but are not limited to, solutions, creams, gels, ointments, foams, suppositories and powders, and may include a variety of additional components such as lubricants, preservatives, carriers and diluents, as well as other active ingredients such as spermacides. Such formulations contain a sufficient quantity of the zinc(II) complex, and are applied to the epithelium of the vaginal mucosa, cervix, anus and/or penis in an amount sufficient to prevent and/or inhibit vital transmission.

In this embodiment, the zinc(II) complexes of the present invention may also serve to prevent and/or inhibit the transmission of sexually transmitted diseases in addition to HIV, including human herpes virus and Hepatitis virus (as well as Chlamydia). The zinc(II) complexes of this invention may also have contraceptive activity.

The zinc(II) complexes of this invention, in addition to inhibiting HIV replication, may also inhibit replication of other viruses. Such viruses include, but are not limited to, human T-cell leukemia (HTLV) I and/or II, human herpes virus (HSV1 and 2), cytomegalo virus (human, hCMV, and murine, mCMV), encephalomyocarditis viruses (HAV, HBV, HCV (EMCV), Epstein Barr virus (EBV), human hepatitis virus (e.g., hepatitis B virus, HBV), Varicella Zoster virus, Rhinovirus, rubella virus, respiratory syncytium virus (RSV), influenza viruses A and B, parainfluenza viruses and adenovirus. One skilled in the art could readily assay the zinc(II) complexes of this invention for their inhibitory activity with regard to these viruses, as well as other viruses.

The following examples are offered by way of illustration, and not by way of limitation.

EXAMPLES

The examples which follow illustrate the preparation, characterization and utility of certain exemplary embodiments of the zinc(II) complexes of the present invention. To summarize the examples that follow: Example 1 illustrates the synthesis and characterization of zinc(II):neocuproine (2:1); Example 2 illustrates the synthesis and characterization of zinc(II):BCDS (2:1); Example 3 discloses methods for monitoring zinc (II) transport into cells by the zinc(II) complexes of this invention; Example 4 discloses methods for assaying the zinc(II) complexes of this invention for their ability to inhibit synthesis of lipid mediators of inflammation; and Example 5 discloses methods for assaying the zinc(II) complexes of this invention for their ability to function as antiviral agents.

Example 1

Synthetic Procedure for Zinc(II):Neocuproine (2:1) and Characterization Thereof Neocuproine hydrate was used as received from Aldrich Chemical Company ("Aldrich"), having the following properties: mp161° C.–163° C.; $^1$H NMR (500MHz, DMSO-d$_6$) δ8.32 (2H, d, J=8.2), 7.85 (2H, s), 7.60 (2H, d, J=8.1), 2.79 (6H, s); $^{13}$C NMR (125MHz, DMSO-d$_6$) δ158.0, 144.6, 136.1, 126.4, 125.3, 123.1, 24.9.

A solution of neocuproine hydrate (4.53 g, 20.0 mmol) in methanol (20 mL) was added to a stirred solution of zinc nitrate hydrate (2.97 g, 10.0 mmol) in methanol (20 mL). A white precipitate formed immediately. This material was collected on a filter, washed with methanol, and dried under vacuum to give 5.66 g (91%) of the monohydrate as a white solid. Recrystallization from aqueous ethanol yielded zinc (II):neocuproine (2:1) as clear plates: mp225.5° C.–226° C.; UV-vis $\lambda_{max}$ (H$_2$O) 226 nm ($\epsilon$=5,185M$^{-1}$ cm$^{-1}$), 276 nm (s=2,992), 298 nm (s=1,196); MS m/z (relative intensity) 546 (M($^{68}$Zn)-(NO$_3$)$^-$)$^+$ (7), 545 (M($^{67}$Zn)-(NO$_3$)$^-$)$^+$ (5), 544 (M($^{66}$Zn)-(NO$_3$)$^-$)$^+$ (10), 542 (M($^{64}$Zn)-(NO$_3$)$^-$)$^+$ (15), 334 (30), 209 (100); HRMS calcd for C$_{28}$H$_{24}$N$_5$O$_3$$^{68}$Zn (M$^+$ less NO$_3$) 546.1128, found 546.1108; calcd for C$_{28}$H$_{24}$N$_5$O$_3$$^{67}$Zn (M$^+$ less NO$_3$) 545. 1150, found 545. 1136; calcd for C$_{28}$H$_{24}$N$_5$O$_3$$^{66}$Zn (M$^+$ less NO$_3$) 544.1140, found 544.1119; calcd for C$_{28}$H$_{24}$N$_5$O$_3$$^{64}$Zn (M$^+$ less NO$_3$) 542.1171, found 542.1138. Anal. calcd. for C$_{28}$H$_{26}$N$_6$O$_7$Zn: C, 53.90; H, 4.20; N, 13.47. Found: C, 54.15; H, 3.99; N, 13.46.

A clear plate of zinc(II):neocuproine (2:1) was mounted on a glass pin with epoxy and transferred to the diffractometer in a nitrogen stream where collection was done at −90° C. The crystals remained clear with little deterioration. The crystal had approximate dimensions of 0.08 mm×0.36 mm×0.36 mm. Twenty five reflections in the range of 24–32 degrees in two-theta were found, and an orientation matrix was determined providing a unit cell with a volume of 2947 Å$^3$. Reduction of data was carried out by the program XCAD4 and all further work was performed using the PC version of Siemens SHELX. The Laue merging R factor was 1.5% for 504 equivalent reflections with a density of 1.37 with four molecules in the unit cell.

Figure 1:
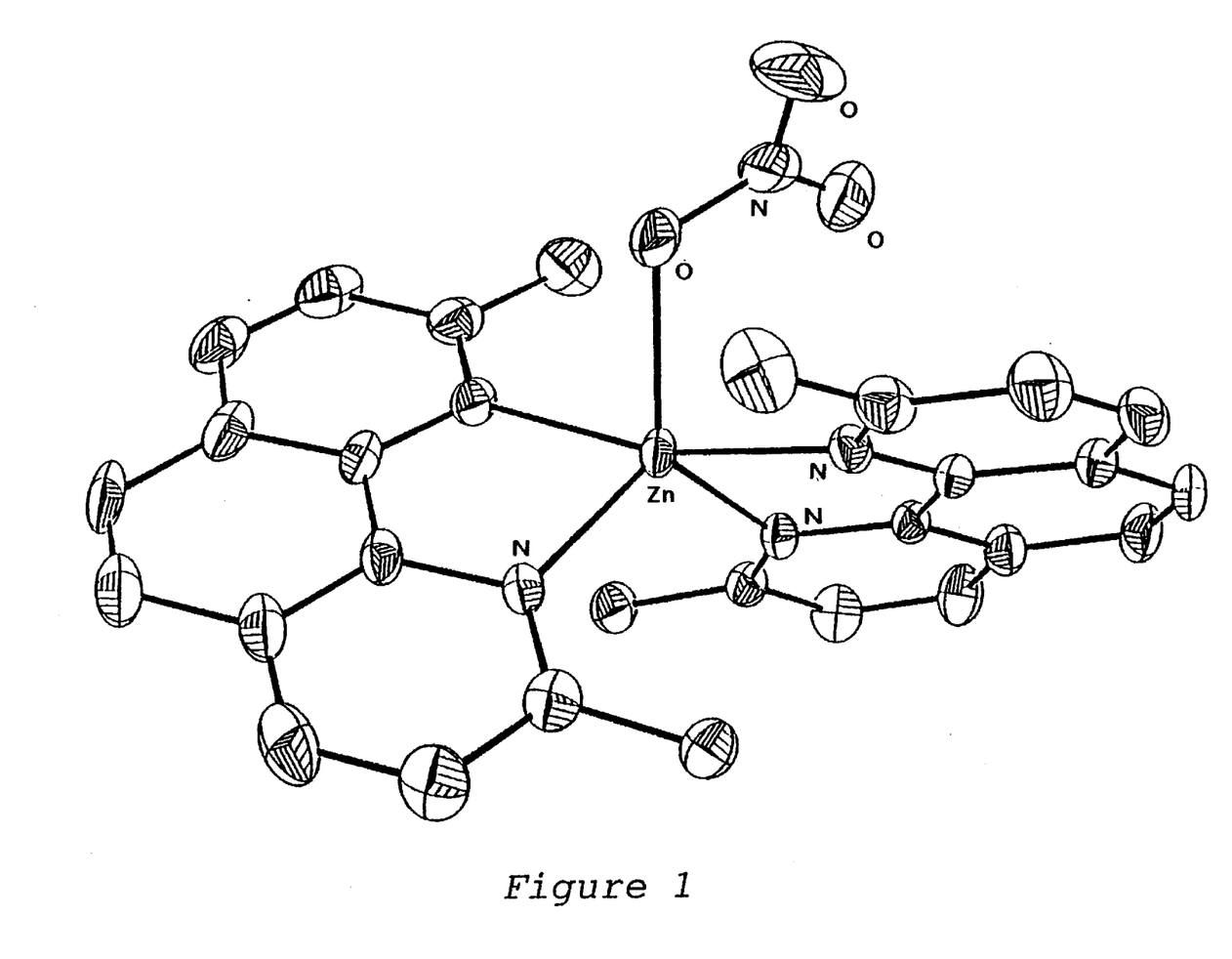
FIG. 1 is the x-ray crystal structure of a representative zinc(II) complex of this invention (i.e., zinc(II):neocuproine (2:1)).

The structure was solved by direct methods, and agreed with the heavy metal location as given by a Patterson function, and the structure was determined from Fourier difference maps. One counter-ion nitrate was found, as well as one nitrate bonded to the zinc atom, giving a five-coordinate complex as illustrated in FIG. 1. Structure determination parameters are summarized in Table 8.

TABLE 8

Structure Determination Summary

A. Crystal Data

| | |
|---|---|
| Empirical Formula | C$_{30}$H$_{32}$N$_6$O$_4$Zn |
| Color; Habit | Clear Plates |
| Crystal Size (mm) | 0.08 × 0.36 × 0.36 |
| Crystal System | Monoclinic |
| Space Group | P2(1)/n |
| Unit Cell Dimensions | a = 11.385(2) Å |
| | b = 15.440(3) Å |
| | c = 17.475(3) Å |
| | β = 106.37(3)° |
| Volume | 2947.3(15) Å$^3$ |
| Z | 4 |
| Formula Weight | 606.0 |
| Density (calc.) | 1.366 Mg/m$^3$ |
| Absorption Coefficient | 0.878 mm$^{-1}$ |
| F(000) | 1264 |

B. Data Collection

| | |
|---|---|
| Diffractometer | Enraf-Nonius CAD4 |
| Radiation | MoKα (λ = 0.71073 Å) |
| Temperature (K.) | 183 |
| Monochromater | Highly oriented graphite crystal |
| 2θ Range | 2 to 50° |
| Scan Type | ω |
| Scan Speed | Variable; 1.5 to 5.5°/min in ω |
| Scan Range (ω) | 0.06° |
| Background Measurement | Stationary crystal and stationary counter at beginning and end of scan, each for 0.5% of total scan time |
| Standard Reflections | 2 measured every 2 hr. |
| Index Range | 0 ≦ h ≦ 13, −1 ≦ k ≦ 18, −20 ≦ 1 ≦ 19 |
| Reflections Collected | 5634 |
| Indep. Reflections | 4949 (R$_{int}$ = 1.85%) |
| Observed Reflections | 3419 (F > 4.0σ (F)) |
| Absorption Corrections | Semi-Empirical |

C. Solution and Refinement

| | |
|---|---|
| System Used | Siemens SHELXTL PLUS |
| Solution | Direct Methods |
| Refinement Method | Full-Matrix Least-Sqrs. |
| Quantity Minimized | Σw (F$_o$ − F$_c$)$^2$ |
| Extinction Correction | X = −0.00018(12), where F* = F[1 + 0.002XF$^2$/sin(2θ)]$^{-1/4}$ |
| Hydrogen Atoms | Riding model, fixed isotropic U |
| Weighting Scheme | w$^{-1}$ = σ$^2$ (F) + 0.0035F$^2$ |
| No. Parameters Refined | 434 |
| Final R Indices (obs. data) | R = 4.59%, wR = 6.81% |

TABLE 8-continued

Structure Determination Summary

| | |
|---|---|
| R Indices (all data) | R = 7.47%, wR = 8.01 |
| Goodness-of-Fit | 1.05 |
| Largest and Mean Δ/σ | 1.515, 0.041 |
| Data-to-Parameter Ratio | 7.9:1 |
| Largest Difference Peak | 0.52 eÅ$^{-3}$ |
| Largest Difference Hole | −0.50 eÅ$^{-3}$ |

Example 2

Synthetic Procedure for Zinc(II):BCDS (2:1) and Characterization Thereof

A stock solution of bathocuproine disulfonic acid disodium salt (BCDS) was prepared by dissolving 27.96 mg of bathocuproine disulfonic acid disodium salt (Aldrich) in 100 ml of HPLC-grade methanol. This solution was further diluted 1:10 in methanol for a final concentration of 0.0495 mM.

Stock $Zn(NO_3)_2$ was prepared by dissolving 1.0764 g of $Zn(NO_3)_2 \cdot 6H_2O$ (Aldrich) in 25 ml HPLC-grade methanol followed by two consecutive 1:10 dilutions in methanol for a final concentration of 2.274 mM.

Bathocuproine disulfonic acid disodium salt (2.0 mL, 0.0495 mM) was placed in a quartz cuvette equipped with a magnetic stir bar and the absorption spectrum was acquired. To the cuvette was added 55 ml of 2.274 mM $Zn(NO_3)_2$ in methanol (1.25 equivalents) using a microliter syringe. The absorption spectrum was acquired with a Hewlett Packard 8452A diode array spectrophotometer and then normalized to correct for the increase in volume.

A spectrum of methanolic $Zn(NO_3)_2$ was also acquired as a control. This spectrum did not show any absorbance at wavelengths greater than 260 nm (data not shown).

Figure 2:
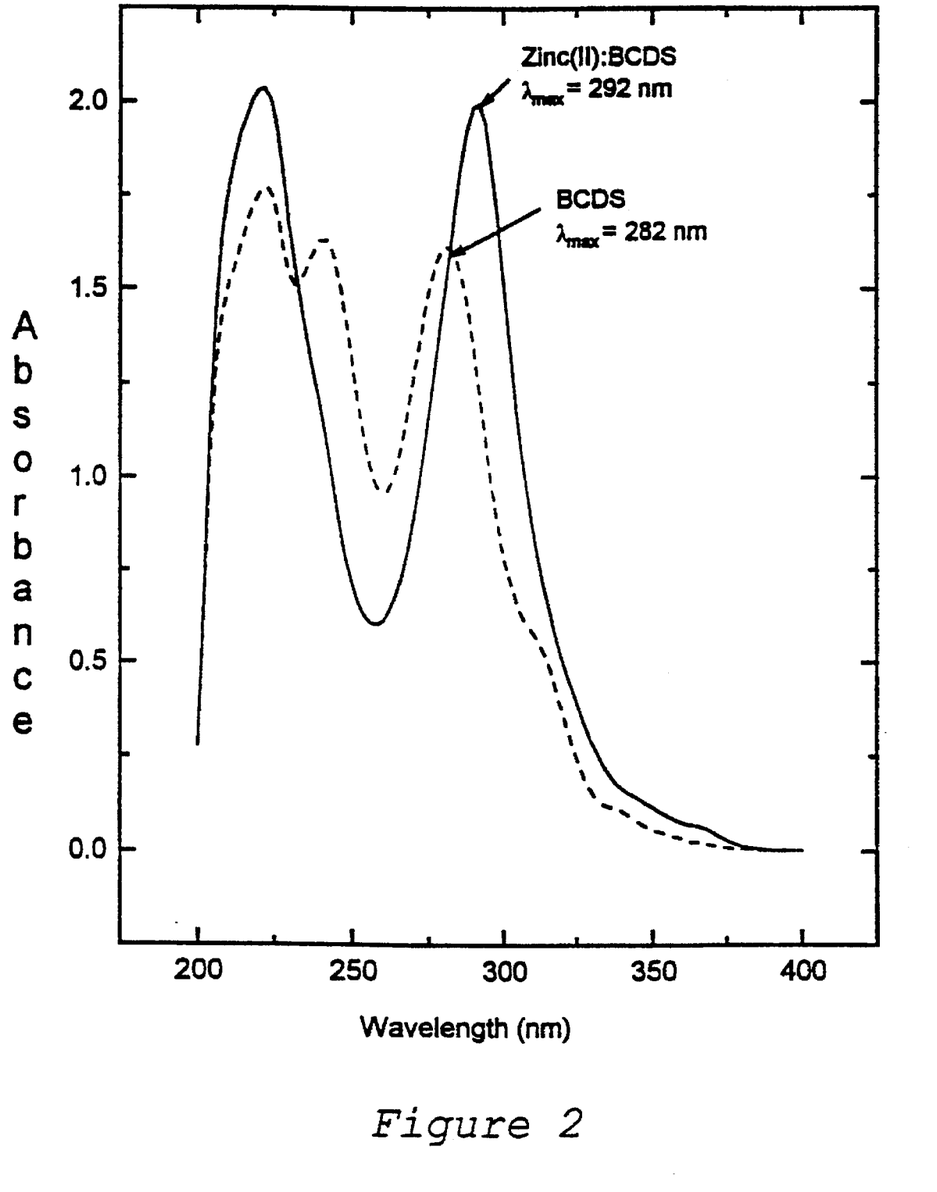
FIG. 2 is the absorption spectrum of a further representative zinc(II) complex of this invention (i.e., zinc(II):bathocuproine disulfonic acid ("BCDS") (2:1)), and presents the absorption spectrum of BCDS for comparison.

The spectra of bathocuproine disulfonic acid disodium salt and Zn-bathocuproine disulfonic acid disodium salt (normalized to the same concentration) are presented in FIG. 2. These data indicates that the observed shift in $\lambda_{max}$ and the corresponding increase in the extinction coefficient at the $\lambda_{max}$ (at wavelengths greater than 260 nm) is due to complexation of the metal atom by bathocuproine disulfonic acid disodium salt.

Example 3

Enhanced Zinc(II) Transport Into Cells Utilizing Zinc (II) Complexes

Detection of metal ion transport into intact cells may be determined utilizing one or more suitable cell lines (such as RBL-1 cells available from American Type Culture Collection, Rockville, Md.). Cells are cultured under established conditions with and without the addition of a zinc(II) complex of this invention. After 24 or 48 hours incubation with the zinc(II) complex of this invention, the culture media is withdrawn and the cells are harvested and washed several times with fresh media or phosphate buffered saline by centrifugation. The resulting cell pellet is then analyzed for total zinc(II) content by, for example, atomic absorption spectroscopy. Based on this procedure, administration of zinc(II) complexes of this invention are shown to enhance and/or facilitate zinc transport into cells.

Example 4

Inhibition of Synthesis of Lipid Mediators of Inflammation

Inhibition of leukotriene synthesis can be conveniently shown by incubating enzymes or cell fractions containing enzymes with compounds which can be converted to leukotrienes by the action of these enzymes. For example, Leukotriene $A_4$ ($LTA_4$) hydrolase (also known as $LTA_4$ synthase) is involved in the formation of $LTB_4$ from $LTA_4$. Leukotriene $A_4$ ($LTA_4$) hydrolase is prepared as a crude fraction from rat lung tissue. The sodium salt of $LTA_4$ is used as a substrate and incubated with the enzyme fraction and a zinc(II) complex of this invention for 1 minute at 37° C. The reaction is terminated by the addition of ice cold methanol. The formation of $LTB_4$ is assessed by a specific RIA (Raclmark et al., J. Biol. Chem. 259: 12339–12345, 1984; Kuhl et al., Prostaglandins 31: 1029–1048, 1986; Izumi et al., Biochem. Biophys. Res. Comm. 135: 139–145, 1986).

The inhibition of the formation of lipid mediators of inflammation can also be determined in intact cells. This assay involves incubation of the rat basophilic leukemia cell line RBL-1 with the zinc(II) complexes of this invention, followed by radioimmunoassay (RIA) analysis for a prostaglandin product of the cyclooxygenase ($PGF_{2\alpha}$) and a leukotriene product of the 5-lipoxygenase ($LTB_4$). Positive and negative controls are also run in each assay (Boschelli et al., J. Med. Chem. 36: 1802–1810, 1993). Using the above methodology, zinc(II) complexes of this invention are shown to inhibit the formation of lipid mediators of inflammation.

Example 5

Anti-Viral Activity

A. Inhibition of HIV

The zinc(II) complexes of this invention may be screened for their ability to inhibit human immunodeficiency virus (HIV) replication using known techniques. For example, HIV virus replication may be monitored using the Cytopathic Effect (CPE) assay disclosed by Bergeron et al. (J. Virol. 66: 5777–5787, 1992). In this assay, the degree of infection is monitored by the appearance of fused cellular membranes ("syncitium"). Alternatively, assays directed to activity of HIV protease may be employed. For example, the assays and techniques disclosed in the following references may be employed: Ashorn et al., Proc. Natl. Acad. Sci. U.S.A. 87: 7472–7476, 1990; Schramm et al., Biochem. Biophys. Res. Commun. 179: 847–851, 1991; Sham et al., Biochem. Biophys. Res. Commun. 175: 914–919, 1991; and Roberts et al., Science 248: 358–361, 1990.

In another method, PHA-stimulated peripheral blood mononuclear cells (PBMC) are infected by $HIV_{IIIB}$ in the presence of the zinc(II) complexes of this invention and cultured in the presence of the zinc(II) complexes of this invention for two weeks. The extent of HIV replication is assayed at 1 and 2 weeks by a p24 antigen capture ELISA assay. More specifically, PBMC are stimulated with PHA for 24 to 72 hours in basal medium, containing RPMI-1640, 10% fetal bovine serum, and 50 µg/mL gentamicin, and then cultured overnight in the presence of 250 units/ml IL-2. Treated PBMC are pelleted by centrifugation and resuspended to $0.75 \times 10^6$/mL in basal medium with appropriate dilutions of the zinc(II) complexes of this invention or with no zinc(II) complexes of this invention added (i.e., control). To each 0.5 mL aliquot of cells, 0.5 mL of appropriate HIV dilution is added. The virus-cell mixture is incubated for 2 hours at 37° C. in a 5% $CO_2$ humidified atmosphere. Following the incubation period, the PBMC are washed twice in phosphate-buffered saline. Cells are resuspended in 5 mL to $7 \times 10^4$ cells/mL in basal medium with (or without) the zinc(II) complexes of this invention. Each cell aliquot is dispensed into four replicate wells of a 48 well tissue culture plate. Cells are fed twice a week with appropriate medium.

At one week and two week culture timepoints the extent of HIV replication is assayed by a p24 antigen capture assay kit (Coulter Corp., Hialeah, Fla.). PBMC are treated with buffered detergent to release viral proteins. The cell extract is absorbed to immunoassay titer plates and p24 is detected by binding of a monoclonal anti-p24 antibody coupled to an enzyme. Following the addition of a chromogenic substrate, the amount of p24 is quantified spectrophotometrically.

B. Inhibition of Other Viruses

Inhibition of other viruses by the zinc(II) complexes of this invention may be assayed by similar techniques as described below:

1. VZV (Varicella Zoster Virus)

HFF cells are maintained in monolayer culture. VZV infections are measured by the plaque reduction technique, in which the virus is suspended in a agarose and distributed over the monolayer of HFF. Areas of destruction (plaques) are determined by removing the agarose and staining the remaining monolayer. Virus yield (plaque forming units) is calculated, and the effect of the test drug is reported as $EC_{50}$, the concentration which reduces viral yield by 50%. Cytotoxicity ($CC_{50}$ for this assay is determined by neutral red (vital dye) uptake on confluent HFF monolayers or by counting cells in rapidly proliferating HFF cells.

2. MV (Measles Virus)

CV-1 cells are cultured in monolayer, and the cytopathic effect (CPE) of the virus id quantitated by vital dye (Neutral Red Uptake). This quantitative method is used for the determination of the $CC_{50}$ also. The point of 50% dye uptake is determined for both the infected ($EC_{50}$ and the uninfected $CC_{50}$ cells), and the ratio determines the SI.

3. PIF-3 (Parainfluenza Type 3 Virus)

MA-104 cells are used with this virus and the same Neutral Red technique for determining ($EC_{50}$, $CC_{50}$ cells, and SI is used as is for MV.

4. RSV (Respiratory Syncytium Virus)

MA-104 cells, and the same Neutral Red Assays are used for RSV as is for MV and PIF-3.

5. IF-A (Influenza A Virus)

The MDCK cell line is used with the same Neutral Red technique as for MV, PIF-3 and RSV.

6. IF-B (Influenza B Virus)

The same technique is used to determine the antiviral effects as with IF-A virus.

7. HCMV (Human Cytomegalovirus)

The same Neutral Red technique is used for HCMV as is for RSV, MV, PIF-3 and the influenza viruses, except that the cells used are HFF.

8. HSV-2 (Herpes Simplex Type 2)

Same technique as HCMV; HFF Cells, Neutral Red for Both $EC_{50}$ and $CC_{50}$, with ratio of $CC_{50}/EC_{50}=SI$ 9. HBV (Hepatitis B Virus)

The HBV virions released by the cells are quantitated (Korba and Milman, *Antiviral Res.* 19: 55, 1992) via DNA hybridization to specific radiolabeled HBV DNA fragments. In this technique, the $EC_{90}$ is determined as the effective concentration of the drug which reduces the yield of HBV DNA by 90%. The $CC_{50}$ is determined for the drug on uninfected cells, and the SI is the ratio $CC_{50}/EC_{50}$.

In the above examples, the abbreviations used are as follows:

HFF—Human Foreskin Fibroblasts, primary fibroblast cultures derived from newborn circumcision skin samples, cultured in vitro;

CV-1—African Green Monkey Kidney Cells cultured in vitro;

MA-104—Embryonic Rhesus Monkey Kidney Cells cultured in vitro;

MDCK—Madin-Darby Canine Kidney Cells cultured in vitro;

2.2.15—Specialized cells for expression of HBV (Korba and Milman, *Antiviral Res.* 15: 217, 1991), 2.2.15 cells are a derivative of Hep G2 Cells (Human hepatocellular carcinoma) which is engineered with a plasmid containing tandem copies of HBV genomes (Sells et al., *PNAS* 84: 1005, 1988; and Sells et al., *J. Virology* 62: 2836, 1987);

$EC_{50}$—Effective Concentration$_{50}$, concentration of a drug which causes a half-maximal biological response (i.e., antiviral effect—the concentration of test substance which restores the culture to 50% viability);

$EC_{90}$—Effective Concentration$_{90}$, concentration of a drug which produces a 90% maximal biological response (for antiviral activity, the concentration which restores the culture to 90% viability);

$CC_{50}$—Cytotoxic Concentration$_{50}$, the concentration of a drug which produces 50% loss of viability, used to describe the cytotoxic or deleterious potential of a drug (also referred to as $IC_{50}$ or Inhibitory Concentration$_{50}$); and SI—Selectivity Index, used to compare compounds with respect to a therapeutic potential by dividing the $EC_{50}$ by either the $CC_{50}$ or the $CC_{90}$.

The zinc(II) complexes of this invention inhibit viral replication in one or more of the above assays, and thus function generally as antiviral agents, and more specifically as antiviral agents to a specific virus. While specific pathogenic viruses are disclosed above for purposes of illustration, other viruses may be assayed by one skilled in the art by known techniques.

From the foregoing, it will be appreciated that, although specific embodiments of the invention have been described herein for purposes of illustration, various modifications may be made without deviating from the spirit and scope of the invention. Accordingly, the invention is not to be limited except as by the appended claims.

I claim:

1. A zinc(II) complex comprising zinc(II) complexed by neocuproine, wherein the ratio of neocuproine to zinc(II) is greater than 1:1.

2. The zinc(II) complex of claim 1 wherein the ratio of neocuproine to zinc(II) is at least 2:1.

3. A zinc(II) complex comprising zinc (II) complexed by bathocuproine disulfonic acid.

4. The zinc(II) complex of claim 3 wherein the ratio of bathocuproine disulfonic acid to zinc(II) ranges from 1:1 to 3:1.

5. A composition comprising a zinc(II) complex of any one of claims 1–4 in combination with a pharmaceutically acceptable carrier or diluent.

* * * * *